United States Patent
Pollack et al.

(10) Patent No.: US 9,927,451 B2
(45) Date of Patent: Mar. 27, 2018

(54) MODULE TRANSPORT SYSTEM THAT CAN BE COMBINED INTO AN AUTOMATION SYSTEM

(71) Applicants: Benjamin Samuel Pollack, Budd Lake, NJ (US); Colin Mellars, Dover, NJ (US); Baris Yagci, Whippany, NJ (US)

(72) Inventors: Benjamin Samuel Pollack, Budd Lake, NJ (US); Colin Mellars, Dover, NJ (US); Baris Yagci, Whippany, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 198 days.

(21) Appl. No.: 14/389,228

(22) PCT Filed: Mar. 29, 2013

(86) PCT No.: PCT/US2013/034551
§ 371 (c)(1),
(2) Date: Sep. 29, 2014

(87) PCT Pub. No.: WO2013/149117
PCT Pub. Date: Oct. 3, 2013

(65) Prior Publication Data
US 2015/0064802 A1 Mar. 5, 2015

Related U.S. Application Data

(60) Provisional application No. 61/617,387, filed on Mar. 29, 2012.

(51) Int. Cl.
G01N 35/02 (2006.01)
G01N 35/04 (2006.01)
G01N 35/00 (2006.01)

(52) U.S. Cl.
CPC ............ *G01N 35/02* (2013.01); *G01N 35/04* (2013.01); *G01N 2035/00326* (2013.01); *G01N 2035/0406* (2013.01)

(58) Field of Classification Search
None
See application file for complete search history.

(56) References Cited

U.S. PATENT DOCUMENTS 5,087,423 A * 2/1992 Ishibashi ............ G01N 35/0092
422/63
5,351,801 A 10/1994 Markin et al.
(Continued)

FOREIGN PATENT DOCUMENTS

| EP | 2 372 370 A2 | 10/2011 |
| WO | 2008/024225 A2 | 2/2008 |
| WO | 2009/068555 A1 | 6/2009 |

OTHER PUBLICATIONS

Hawker, CD. Laboratory Automation: Total and Subtotal; Journal of Clinics in Laboratory Medicine 27 (2007); p. 749-770.*
(Continued)

*Primary Examiner* — Sean E Conley
*Assistant Examiner* — Benjamin R Whatley

(57) ABSTRACT

An integrated automation system for use in transporting samples between modules, the system can include a plurality of modules configured to be connected to one another for processing samples, each of the plurality of modules having an internal transport system. Each internal transport system includes one or more periphery track portions integrated within a respective module, each of the periphery track portions having two ends and one or more transverse track portions integrated within the respective module, the one or more transverse track portions intersecting at least one of the one or more periphery track portions. The internal transport systems can be configured to connect to one another via one (Continued)

end of the two ends connecting to one end of the two ends of adjacent periphery track portions, thereby forming a continuous periphery track running through and connecting the plurality of modules. Samples are transported along the continuous periphery track and the one or more transverse track portions. The continuous periphery track and the one or more transverse track portions form a plurality of paths along which the samples are transported.

20 Claims, 12 Drawing Sheets

(56) References Cited

U.S. PATENT DOCUMENTS

| | | |
|---|---|---|
| 5,988,857 A | 11/1999 | Ozawa et al. |
| 6,056,106 A | 5/2000 | van Dyke, Jr. et al. |
| 6,429,016 B1 | 8/2002 | McNeil |
| 6,520,313 B1 | 2/2003 | Kaarakainen et al. |
| 7,597,848 B1* | 10/2009 | Ameling .............. G01N 35/028 422/504 |
| 2002/0028157 A1* | 3/2002 | Takahashi ............ G01N 35/026 422/65 |
| 2003/0044319 A1* | 3/2003 | Itoh ........................ G01N 35/04 422/63 |
| 2008/0038827 A1 | 2/2008 | Miller et al. |
| 2008/0063496 A1* | 3/2008 | Bufano ............. H01L 21/67017 414/331.01 |
| 2009/0117620 A1 | 5/2009 | Fritchie et al. |
| 2011/0076194 A1* | 3/2011 | Kitagawa ............. G01N 35/026 422/65 |
| 2011/0306051 A1* | 12/2011 | Belz .................... C12N 15/1006 435/6.12 |
| 2012/0301358 A1* | 11/2012 | Haechler ............. G01N 35/026 422/64 |
| 2014/0370608 A1* | 12/2014 | Gelbman ................ B01L 3/545 436/47 |

OTHER PUBLICATIONS

PCT International Search Report and Written Opinion dated Jul. 9, 2013 (9 Pages).

Extended EP Search Report dated Jun. 6, 2016 of corresponding European Application No. 13768902.2, 4 Pages.

* cited by examiner

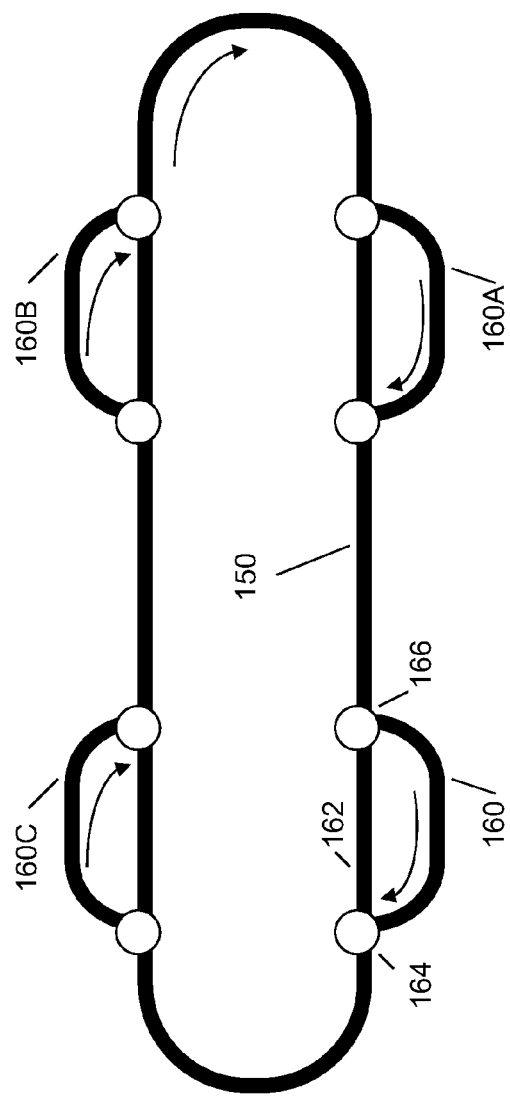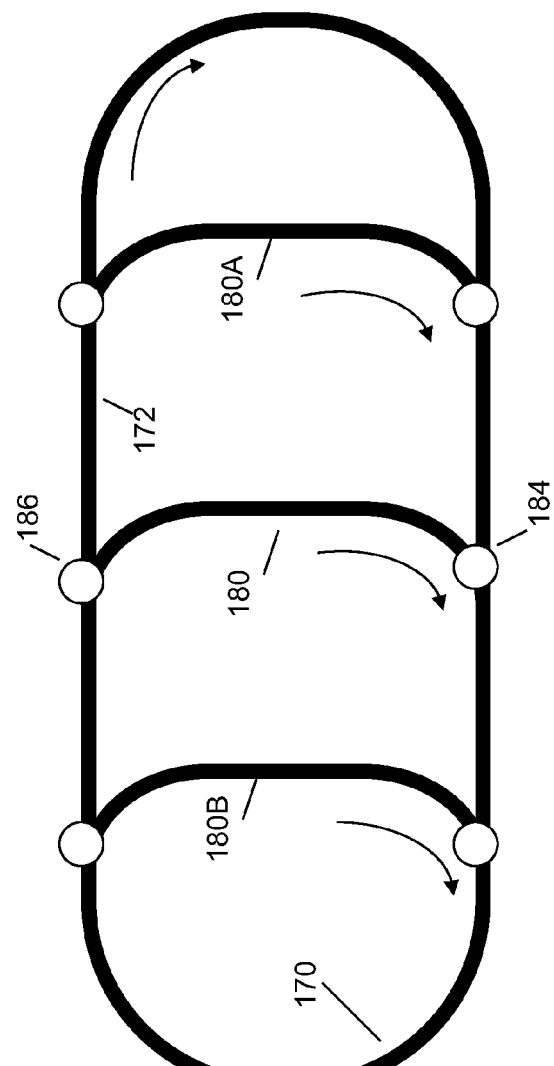

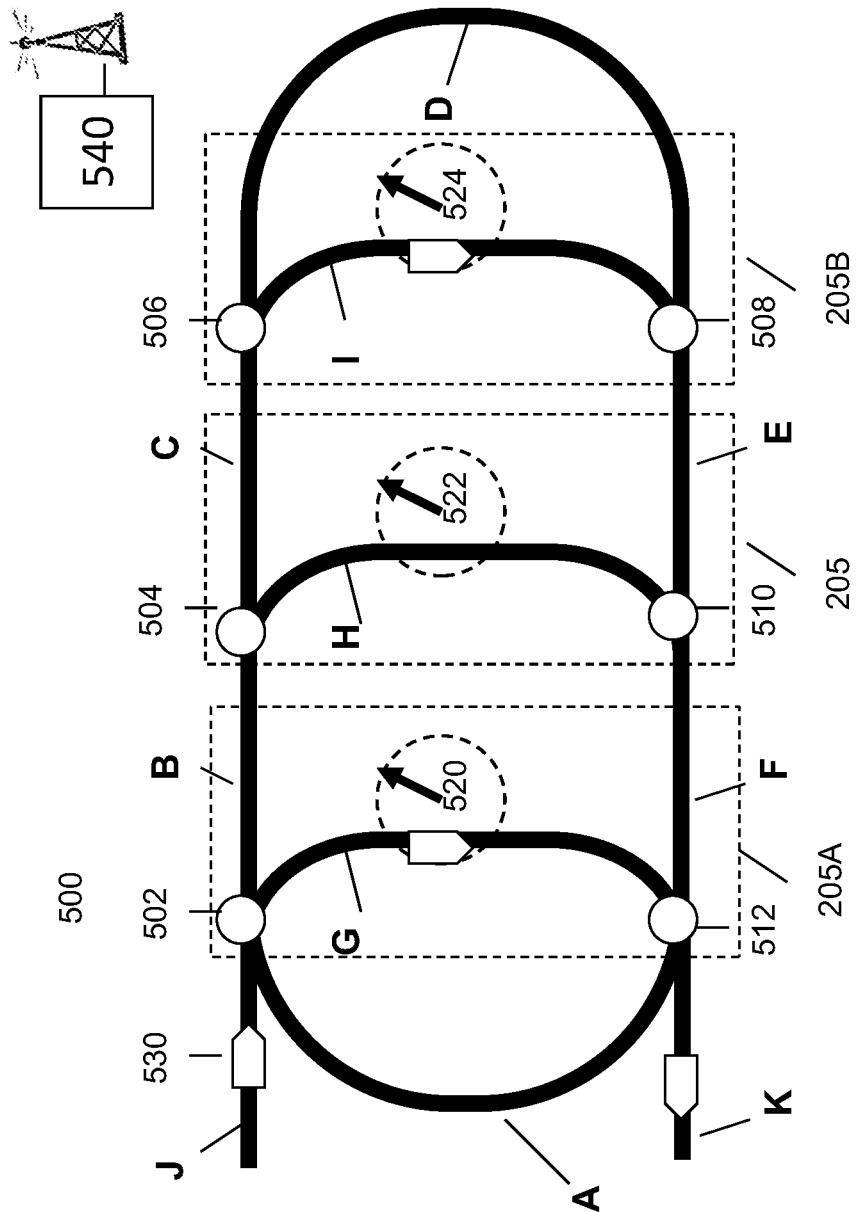

US 9,927,451 B2

MODULE TRANSPORT SYSTEM THAT CAN BE COMBINED INTO AN AUTOMATION SYSTEM

CROSS-REFERENCE TO RELATED APPLICATIONS

This application claims priority to U.S. provisional application Ser. No. 61/617,387 filed Mar. 29, 2012, which is incorporated herein by reference in its entirety.

TECHNOLOGY FIELD

The present invention relates in general to an automation system for use in a laboratory environment and, more particularly to systems and methods for transporting patient samples for in vitro diagnostics in a clinical analyzer via active transport devices. Embodiments of the present invention are particularly well suited, but in no way limited, to internal transport systems in modules within an analyzer that can be linked to the internal transport system of one or more other modules to form an integrated automation system with little or no additional hardware footprint.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers.

Some traditional track systems are designed to transport samples from one fully independent module to another standalone module. This can minimize the constraints on the design and implementation of the individual modules, allowing each module to handle each sample in its own way once receiving the sample from the automation system. This approach may also allow a single module to be sold as a standalone analyzer or analyzer station, allowing later purchase of a separate, external automation system as a lab grows. However, this approach can create significant inefficiencies and barriers to full feature integration. A standalone module must maintain an internal distribution system to transport samples from one subassembly to the next. This distribution system may be somewhat redundant when the module is attached to an automation track. That is, multiple systems are then involved in moving a sample at different points in the workflow.

Redundant hardware can increase cost, enlarge footprint, add complexity, and reduce reliability. Generally, a module's subassemblies and algorithms are optimized around the physical layout and capabilities of its internal distribution system. Samples that are accessed from the track are often processed less efficiently or with fewer features than samples that are loaded directly on the module.

There are several conventional approaches for transporting samples between independent sample processing modules. For example, the IMMULITE® immunoassay system with the VersaCell® automation system manufactured by Siemens includes physical transfer of the sample vessel between an automation track and an analyzer module. By physically transferring the sample from a track to the internal distribution system of the module, the IMMULITE instrument is able to retain full-featured processing capabilities for track based samples. However, this adds even more redundant hardware and imposes additional processing time penalties as sample vessels must be removed from and placed onto automation tracks or internal motion mechanisms. For example, a robot arm or the like may be needed to transfer a sample vessel from an external automation track to the internal motion mechanisms.

Another example includes Siemens' Dimension Vista® system. Analyzer modules in the Dimension Vista® system include a linear track on the back that can be linked with the tracks of another analyzer module to double throughput. By linking the track on the back of modules, the Vista® instrument essentially acts like several independent analytical modules united by a common internal distribution system for inputting and outputting samples. This is effective for the combined modules, but it does not scale easily. Furthermore, a linear track on the back of the module does not fully integrate modules within a workflow, as analyzer modules handle separate samples, while allowing a common input and output lane.

SUMMARY

Embodiments of the present invention may address and overcome one or more of the above shortcomings and drawbacks by taking a modular approach to automation systems, whereby modules include portions of an automation system that can be linked to for a larger automation system in a multi-module mode or used to provide local motion systems when operated in a standalone mode. This technology is particularly well-suited for, but by no means limited to, transport mechanisms in an automation system for use in an in vitro diagnostics (IVD) environment.

According to one embodiment of the invention, an integrated automation system for use in transporting samples between modules includes a plurality of modules configured to be connected to one another for processing samples. Each of the plurality of modules includes an internal transport system that includes one or more periphery track portions integrated within a respective module. The periphery track portions have two ends. One or more transverse track portions are integrated within the respective module and intersect at least one of the periphery track portions. The internal transport systems are configured to connect to one another via one end of the two ends connecting to one end of the two ends of adjacent periphery track portions, thereby forming a continuous periphery track running through and connecting the plurality of modules. The samples can be transported along the continuous periphery track and the one or more transverse track portions, the continuous periphery track and the one or more transverse track portions forming a plurality of paths along which the samples are transported.

According to one aspect of some embodiments each of the plurality of modules further comprises a first side, a second side opposite the first side, a front side extending between the first side and the second side, and a back side opposite the front side and extending between the first side and the second side, wherein the first side and the second side are spaced apart from one another, wherein the front side and the back side are spaced apart from one another. Each of the plurality of modules comprises two periphery track portions, a first periphery track portion extending from the first side to the second side proximate the front side of the respective module, and a second periphery track portion extending from the first side to the second side proximate the back side of the respective module. Each of the one or more transverse track portions integrated within the respective module extends between and intersects the first periphery track portion and the second periphery track portion, and plurality of paths formed by the continuous periphery track and the one or more transverse track portions comprise a plurality of continuous loops when the internal transport systems of respective modules are connected to one another.

According to another aspect of some embodiments, the integrate automation system can include one or more dedicated return lanes. Each dedicated return lane includes two return ends and is configured to be connected to the continuous periphery track via a first of the two return ends and a second of the two return ends connecting to one end of respective adjacent periphery track portions. According to yet another aspect of some embodiments, the integrated automation system can include one or more dedicated modules integrated within one or more of the one or more dedicated return lanes and including one or more components offloaded from one or more of the plurality of modules.

According to still another aspect of some embodiments, the intersection of the one or more transverse track portions with at least one of the one or more periphery track portions can include (i) a sharp intersection, (ii) a gradual curved intersection, or (iii) a double-branch gradual curved intersection. The intersection of the one or more transverse track portions with at least one of the one or more periphery track portions can include the gradual curved intersection, where the samples are transported unidirectionally. The intersection of the one or more transverse track portions with at least one of the one or more periphery track portions can include the double-branch gradual curved intersection, where the samples are transported bidirectionally.

According to another aspect of some embodiments, at least a subset of the plurality of modules can include in vitro diagnostics modules, and wherein the samples include patient samples. According to yet another aspect of some embodiments, the modules can include one or more of: (i) a sample handling module; (ii) an immunoassay module; and (iii) a clinical chemistry module. According to still another aspect of some embodiments, each of the plurality of modules can be capable of stand-alone operation when not connected to other of the plurality of modules.

According to another aspect of some embodiments, a plurality of selected samples can be diverted to one of the one or more transverse track portions for processing by an instrument on the respective module. According to yet another aspect of some embodiments, a prioritized sample can be diverted to one of the one or more transverse track portions for processing by the respective module by transporting samples preceding the prioritized sample along the continuous periphery track.

In another embodiment of the invention, a method of transporting samples between modules includes providing the internal transport systems disclosed herein.

In another embodiment of the invention, an analyzer module for use in an IVD environment includes a plurality of substantially parallel automation surfaces running from one side of the analyzer module to another side of the analyzer module and one or more internal automation surfaces that intersect the plurality of substantially parallel automation surfaces that are configured to provide access to one or more analyzer instruments for samples that move along the one or more internal automation surfaces. The analyzer module is configured to enable operation in a standalone mode to form a local automation system, whereby samples traverse the plurality of substantially parallel automation surfaces and the one or more internal automation surfaces to reach the one or more analyzer instruments. The analyzer module is further configured to enable operation in a multi-module mode whereby the traverse the plurality of substantially parallel automation surfaces are coupled to corresponding automation surfaces of other analyzer modules to form a multi-module automation surface.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 9 is a diagrammatic view of exemplary routes in an exemplary track configuration that can be used for navigation of sample carriers in certain embodiments.

DETAILED DESCRIPTION OF ILLUSTRATIVE EMBODIMENTS

Figure 1:
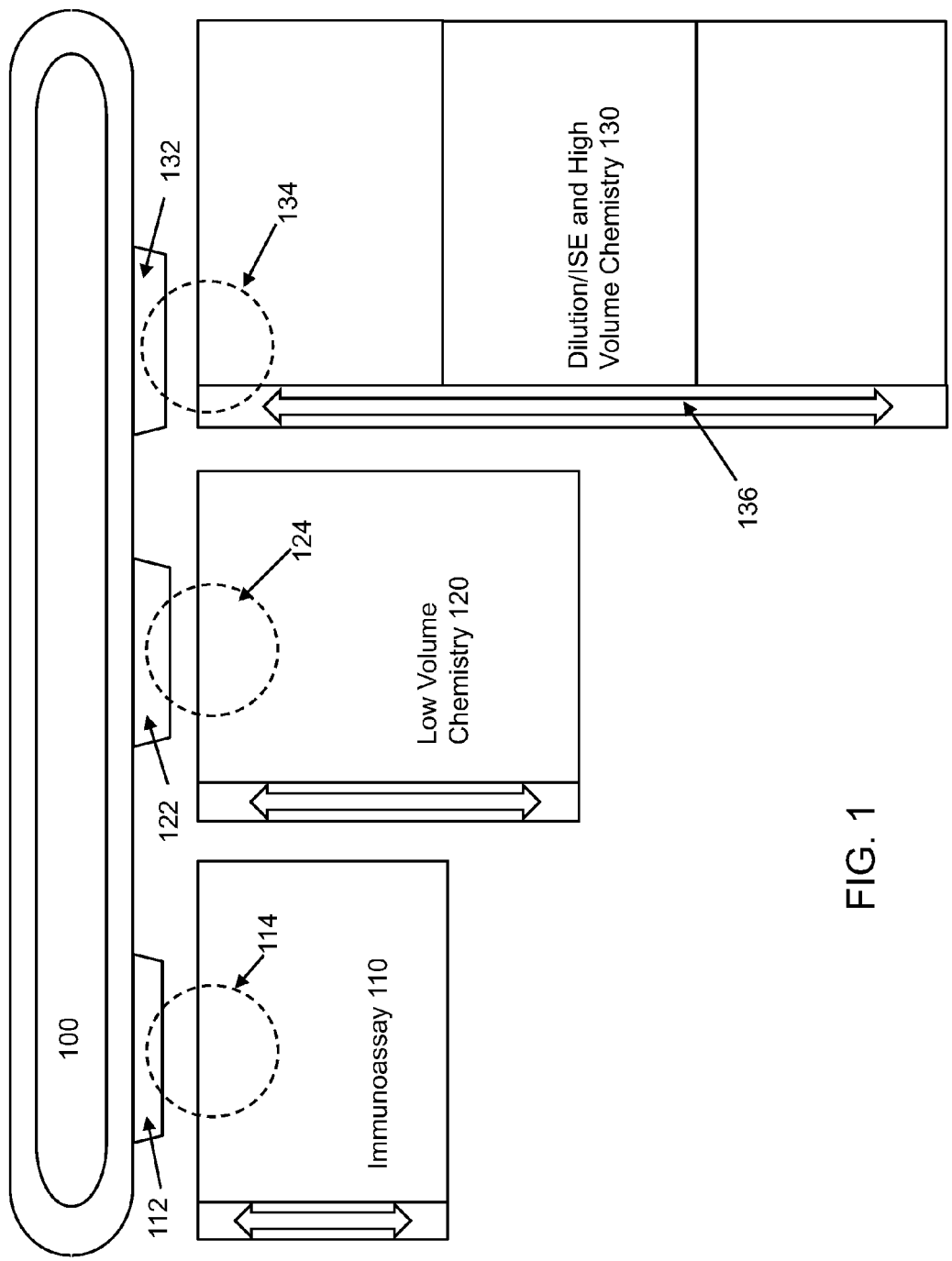
FIG. 1 is a top view of an exemplary clinical chemical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system, on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in analyzer module may include, but are not limited to a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and by extension fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include on-board intelligence that allows carriers to be self-guided between points in an automation system. In some embodiments, carrier can include onboard components that provide motive forces, while in others, motive forces may be provided by an automation surface, such as a track. In some embodiments carriers move along automation tracks which restrict motion to a single direction (e.g., fore and aft) between decision points. Carriers may be specialized to a given payload in an IVD environment, such as having a tube holder to engage and carry a sample tube or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or plurality of combinations of payloads that differ by size, weight, form factor, and/or content. The trajectories of each independently controlled carrier may be limited by a motion profile which includes; maximum jerk, acceleration, direction, and/or speed for the carrier while moving in the automation system. The motion profile can limit or define the trajectory for each carrier independently. In some embodiments a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic or trajectory rules. Some intelligent carriers may also include onboard sensors to assist onboard processors to route the carrier or make decisions responsive to the carrier's environment. Some intelligent carriers may include onboard components, such as motors or magnets that allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel, or more generally in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing, (e.g., a re-capper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: a processor may refer to one or more processors and/or related software and processing circuits. This may include single or multicore processors, single or multiple processors, embedded systems, or distributed processing architectures as appropriate for implementing the recited processing function in each embodiment.

Pullouts, sidecars, offshoot paths: These terms may be used to refer to track sections that are off the main portion of a track system. Pullouts or side cars may include chords, parallel tracks, or other suitable means for separating some carriers from a primary traffic pattern. Pullouts or side cars may be configured to facilitate physical queues or allow certain carriers to stop or slow down without disrupting traffic on a main track section.

Samples: Samples refer to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each Module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of or be separate from an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention may be directed to modules that can be linked with other modules to provide a modular analyzer, and which may be further configured in a standalone mode. This may allow a lab to buy equipment that is scalable, allowing a small lab to operate an analyzer module as a standalone analyzer, but also allowing flexibility by scaling as the lab grows. By using the integrated automation system of each module to link to other modules, multiple modules may form a single analyzer with a single automation system with little or no additional hardware or footprint beyond the space taken each module.

Each module can include integrated automation tracks that facilitate movement of sample vessels within the module. This may allow a module's internal transport system to be linked to the internal transport system of one or more other modules to form an integrated automation system with little or no additional hardware/footprint—completely eliminating the need for a separate, discrete track. This can save space by eliminating redundant motion systems in a module. For example, some prior art analyzers allows modules to operated in a standalone mode or be linked with other modules via an automation system. However, the automation system used would typically be separate (and possibly added on) from the internal motion systems used by the module to move samples within the module (e.g., carousels that move samples between local pipette stations within the module).

The internal motion system of an analyzer can be configured to facilitate motion of samples in standalone mode and as part of a larger integrated motion system by providing an automation track integrated into an analyzer that includes at least two periphery transport lanes that run the length of the module (e.g., one in the front and one in the back) connected by at least one transport lane that runs the width of the module (e.g., running from the front to back or vice versa from the perspective of an operator). This allows movement of a sample to a large part of the area of the module, and provides natural input and output locations to the automation track. Furthermore, when a lab adds additional modules or additional track sections that may provide a return track between the ends of the periphery transport lanes, a plurality of loops or paths may be available for samples to take when traveling around the transport system.

For example, in a multi-module setup, the periphery transport lanes may be used to pass samples through a first module to a second module for processing. Samples that are processed by the first module may be diverted to the transverse/widthwise transport lane that forms a path between the two peripheral transport lanes. Alternatively, the first module may also be configured in a standalone mode, whereby one periphery lane acts as an input lane, while the other acts as an output lane. The transverse lane may join the input and output lanes, and allow the samples to be moved to various interaction points for processing. By providing an internal transport system that may be configured as an automation system for multiple modules, hardware costs and redundancy may be reduced.

Usually, samples need to undergo many different types of testing in an automated clinical analyzer (analyzer), which may not be available in a single testing station or module. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

An exemplary track geometry, for use in transporting samples within an analyzer typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. In typical prior art setups, track 100 and sidecars 112, 122, and 132 are separate automation hardware that can be added externally to modules, meaning that prior art configurations can take additional floor space and incur additional delays.

At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload with the IVD environment, such as fluid samples, reagents, or waste. Fluids, such as patient samples can be placed in a container or vessel, such as a test tube, vial, cuvette, etc. that can be transported by a carrier. Carriers, and by extension payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3A:
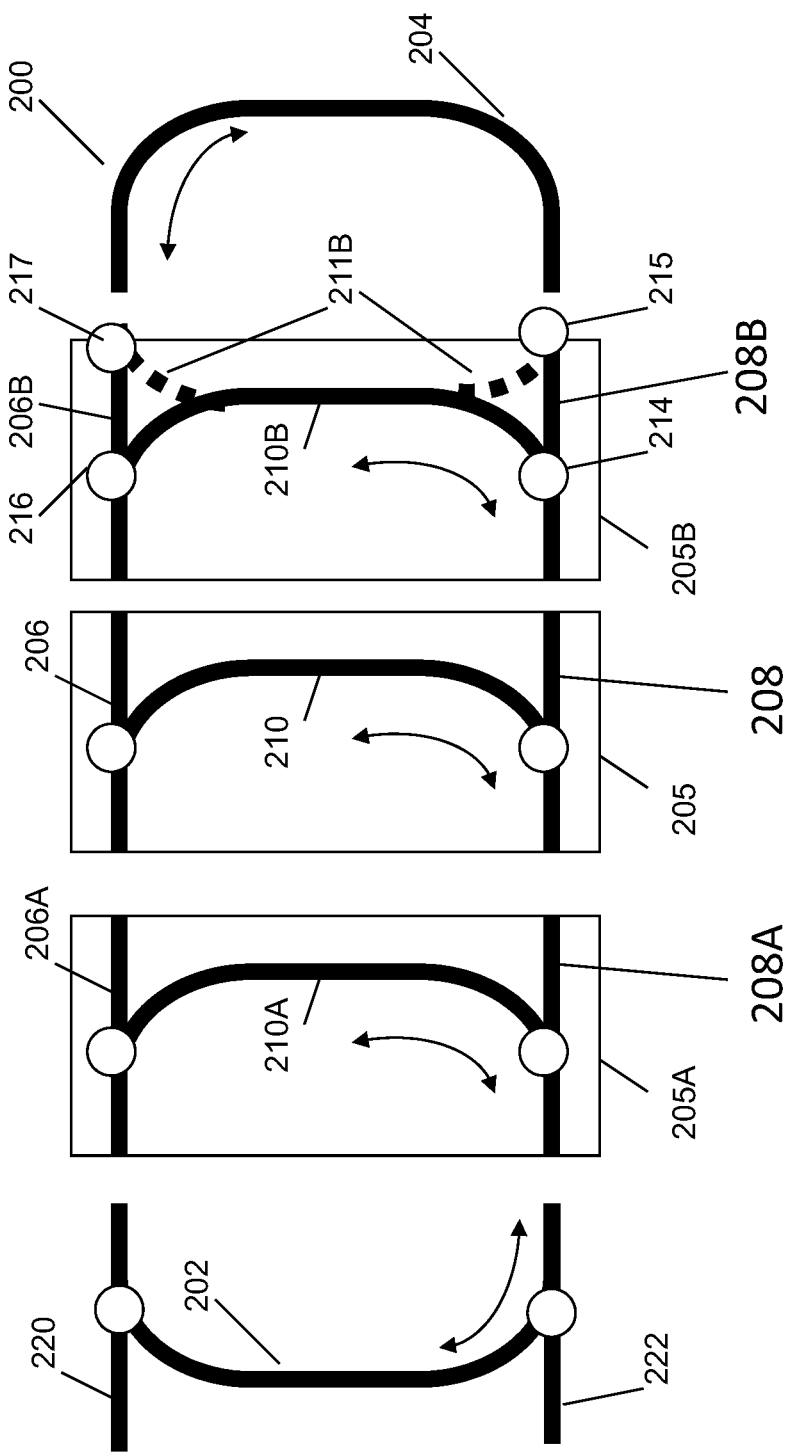
FIG. 3A is a diagrammatic view of an exemplary modular track configuration that can be used with the embodiments disclosed herein.

FIG. 3A shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station or module can include its own queuing logic and may be simplified to eliminate unnecessary redundant internal motion systems. The portion of the automation system within a module may sometimes be referred to as a transport system. A transport system used in some embodiments may be configured to allow a standalone mode where the transport system provides means for moving samples to/from an input and output point and one or more interaction points, such as aspiration points within the module, effectively acting as a local automation system. Furthermore, the transport systems used with some embodiments can be linked between modules to provide a larger integrated automation system.

With respect to FIG. 3A, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by external track segments 202, 204, and internal periphery track segments 206, 206A, 206B, 208, 208A, and 208B, which run lengthwise. Within the analyzer modules 205, 205A, and 205B, internal paths 210, 210A, and 210B, which may be substantially transverse/widthwise, form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

In some embodiments, enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3A and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

Figure 3B:
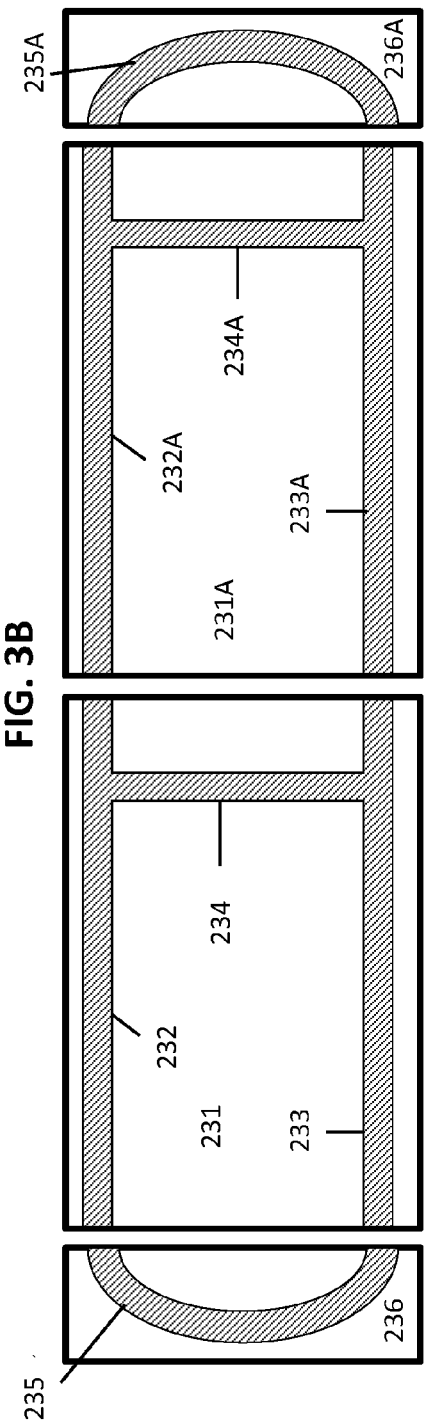
FIG. 3B is a diagrammatic view of an exemplary modular track configuration that can be used with the embodiments disclosed herein.

FIG. 3B shows additional details of an exemplary transport system that may be used with some embodiments from a top-down perspective. Module 231 includes two periphery tracks 232 and 233 (sometimes referred to as transport lanes) that run the length of the front and back of module 231. Module 231 may include analyzer hardware including stations and pipettes that may interact with samples. Between the two periphery lanes, a substantially widthwise/transverse lane 234 allows samples to move between tracks 232 and 233. Similarly, module 231A includes two periphery tracks/transport lanes 232A and 233A that run the length of the front and back of module 231A. Module 231A may include analyzer hardware including stations and pipettes that may interact with samples. Between the two periphery tracks, a substantially widthwise/transverse lane 234A allows samples to move between tracks 232A and 233A. Modules 231 and 231A may be joined to form a larger analyzer. Periphery tracks 232 and 232A can be joined to form a larger periphery track at the back of the analyzer, while periphery tracks 233 and 233A may be joined to form a larger periphery track at the front of the analyzer. Meanwhile, transverse tracks 234 and 234A provide parallel transverse lanes to allow samples multiple paths between the two periphery tracks. It will be appreciated that more than two modules may be linked, and an analyzer may include an reasonable number of linked modules.

External track sections may be added to the ends of periphery tracks to provide additional return paths, allowing periphery paths to form a continuous loop, while transverse paths form sidecars to this main loop. This can allow the main loop to provide a default traffic pattern for samples moving throughout the analyzer while transverse paths may provide local access to analyzer stations or provide shortcuts for samples when there is no queue on a transverse path. In this example, peripheral units 236 and 236A provide periphery return tracks 235 and 235A, respectively. Peripheral units 236 and 236A may be as simple or complex as the application requires, and may be designed to limit the additional floor space taken up by these periphery units. In this example, there are four widthwise paths between the two main periphery tracks, including tracks 235, 234, 234A, and 235A.

The system shown in FIG. 3B illustrates an example of an integrated automation system for use in transporting samples between modules that includes a plurality of modules configured to be connected to one another for processing samples. Each of the plurality of modules 232 and 232A have an internal transport system with two (although some embodiments may include any reasonable number, including one or more) periphery track portions 232 and 233 (or 232A and 233A) integrated within the respective module. Between the periphery track portions, a substantially transverse track portion 234 (or 234A) provides a path by intersecting at least one of the periphery track portions. It should be appreciated that any reasonable number of transverse track portions may be used, allowing multiple paths to be created. The internal transport systems of each module are configured to connect to one another via one end of the ends of the periphery track sections, allowing connection of adjacent periphery track portions. This may form a plurality of continuous periphery tracks running through and connecting the plurality of modules. By using peripheral modules, such as 236 and 236A, periphery return tracks can allow a plurality of periphery tracks to form a continuous periphery loop. Samples (carried by carriers, such as pucks or other carriers described throughout) can then be transported along the continuous periphery track and the one or more transverse track portions. This can provide a plurality of paths along which the samples can be transported. If a module is not using its processing queue on a local transverse lane, then the lane can be dynamically repurposed as a bypass lane by the integrated automation system. This allows the rerouting capabilities of the integrated system to intrinsically scale as more modules are added. In order to increase the efficiency of the main pathways, an (optional) dedicated return lane 235 and/or 235A can be attached to either or both ends of the integrated automation system. This helps ensure that a closed loop path will always exist even if all of the sample queues are occupied.

It should be understood that the exemplary module 231 in FIG. 3B is generally rectangular and the internal lanes/tracks are generally perpendicular and parallel. However, other shapes are also contemplated and may be utilized to practice some embodiments. In the embodiment shown in module 231, there is a front side (bottom of page) back side (top of page) and a left and right side. Periphery tracks 232 and 233 run from the right to left side of the module, while transverse track 234 runs between these periphery tracks generally in the direction between the front and back of the module.

Modules may be linked by placing them side-by-side, such that the right side of module 231 is placed adjacent the left side of module 232A, and the ends of the periphery tracks are placed adjacently. Tracks 232 and 232A and tracks 233 and 233A may be mechanically coupled through any conventional means, providing access to move sample carriers out of module 231 and off of track 232 and into module 230 1A and onto track 232A by placing the end of track 232 substantially adjacent to the end of track 230 2A, carriers may be moved substantially seamlessly between the two track portions, allowing track portions 232 and 232A to act as one longer continuous periphery track. Furthermore, it should be appreciated that multiple transverse tracks, such as track 234 may be placed substantially transverse to periphery tracks 232 and 233 to provide a plurality of paths between these track sections. This may allow one or more loops with in module 232, as well as allowing other loops within the analyzer that may be formed via transverse tracks (such as 234A) in other modules or peripheral return tracks, such as track 235. Peripheral return tracks may be coupled to periphery tracks in modules by aligning the two ends of the tube periphery tracks with the two ends of the peripheral return track, thus joining the two periphery tracks via the peripheral return track.

It should also be appreciated that integrated tracks need not be permanently integrated into the structure of an analyzer module. For example, tracks may be removable from the module to allow the module to be serviced or installed. In some embodiments, tracks that may be referred to as internal or integral are freely upgradeable or replaceable. In some embodiments, these tracks may be removed when moving, servicing, or installing modules. Integral tracks can be considered part of the operable portion of a module that facilitate a standalone mode or a linked multi-module mode, even if they can be physically removed when the module is not operating.

In some embodiments, peripheral return track may be part of a peripheral return module that may include necessary hardware and software for operating the modules in a larger linked automation system. For example, modules 231 and 231A may include the necessary hardware and software for operating in standalone mode. However, when multiple modules are joined together to include a continuous periphery track in automation mode, an automation controller that controls the switching decisions of sample carriers on automation track and provides sensors necessary to detect identities of samples or characterize samples and carriers, etc. may be necessary, in addition to the hardware in the analyzer modules that is used to operate the periphery track and transverse tracks in standalone mode. This additional automation control hardware and software may be provided inside of a peripheral return track module, such as module 236. Meanwhile, standalone mode hardware may be used in a linked automation mode to facilitate local motion within the module as samples traverse the lanes in the module.

Figure 3C:
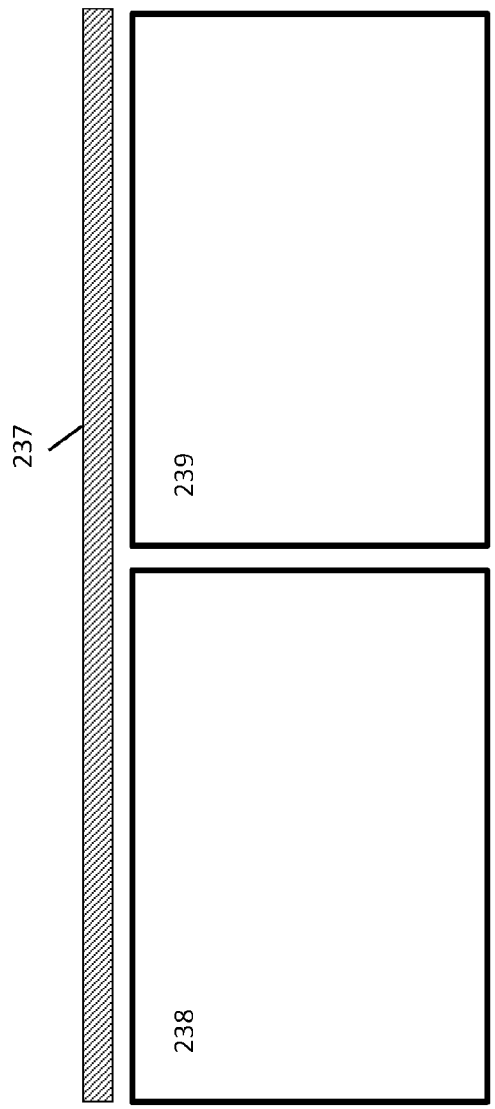
FIG. 3C is a diagrammatic view of an exemplary modular track configuration that can be used with the prior art.

In contrast to the modular system shown in FIG. 3B, FIG. 3C shows an exemplary prior art automation system. Modules 238 and 239 may be joined by a linear track 237. Track 237 is not integrated into modules 238 or 239, and is instead an external automation system that must be mounted to the back of the two modules. This can take up additional floor space on the backside of an analyzer, and may limit the amount of samples that may traverse the automation system. For example, a single track 237 may not easily be used to provide random access for multiple samples moving from one side to the other. Furthermore, if track 237 is a unidirectional track, the track may not provide any means for providing random access between modules, as samples must always flow from one module to the other, in the order in which they are input, limiting the configurability of input and output lanes and assignment of tests between multiple modules. While a single track may be bogged by the delay of a single sample, the transport system shown in FIG. 3B provides multiple paths between all points in the transport system, allowing samples to be rerouted or more efficiently routed. Similarly, unlike the transport system in FIG. 3B, samples must be moved from the automation track 237 and placed into local transport mechanisms within analyzers to 238 and 239 to be moved to other portions of these analyzers not accessible to track 237. This can result in requiring redundant hardware to be designed into modules 238 and 239 in the sense that motion systems other than the automation system must be provided by the modules. The transition from the automation system to local motion systems may be slow and introduce large amounts of latency, limiting the amount of samples that may traverse each module or the automation system. From a design standpoint, the automation system in FIG. 3C reflects an approach whereby modules are designed to be standalone units first, and automation is designed to be an external accessory. The accessory automation hardware can be expensive, as long lengths of automation track must be added to convert standalone modules to a linked automated analyzer. It should also be appreciated that the embodiment shown in FIG. 3B is not necessarily wider than the exemplary prior art in FIG. 3C. For example, by integrating the track into each module, additional systems, such as systems for transferring samples from an external automation track may be eliminated, resulting in a more compact module. Furthermore, because the transport systems are integrated into the module, the transport systems may be placed at any reasonable height within the analyzer, which may allow the automation track to be placed without requiring additional floor space for the analyzer, such as by placing the automation tracks within the analyzer above other components. Similarly, peripheral units 236 and 236A are not necessarily shown to scale and may be narrow and may further be configured to be supported by adjacent modules, which may allow additional lab equipment to be placed underneath periphery return tracks 235 and 235A.

Figures 4A, 4B:
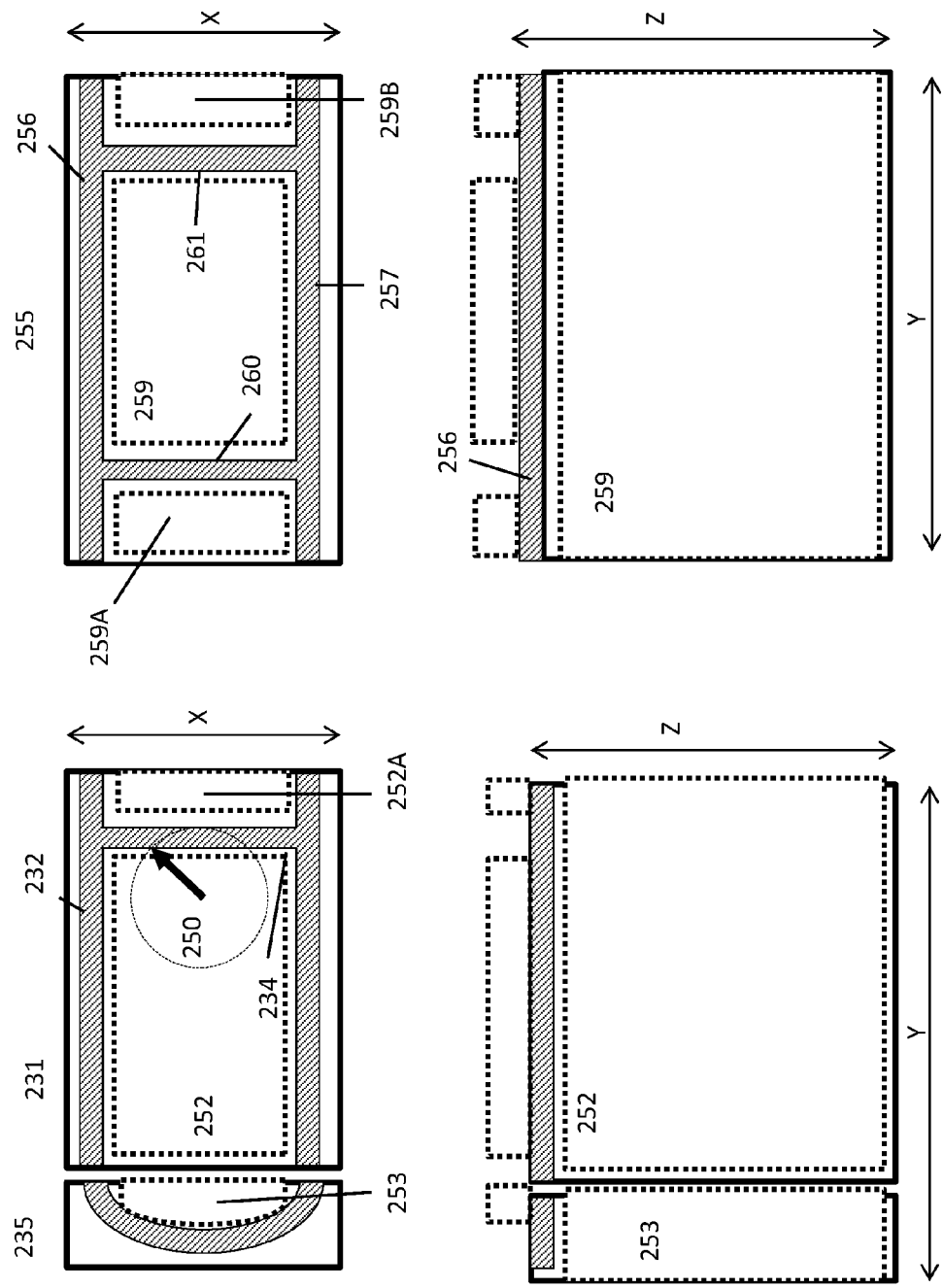
FIGS. 4A and 4B are top and side perspectives of exemplary modules that may be used with some embodiments.

FIG. 4A shows top and side views of an exemplary module for use with some embodiments and an exemplary peripheral unit. Exemplary module 231 includes peripheral tracks, such as periphery track 232 and one or more transverse tracks, such as track 234. A pipette, such as pipette 250 may be placed within the module to interact with samples along the internal automation tracks. For example, pipette 250 interacts with samples while they are on transverse track 234. This may allow samples to traverse the periphery tracks freely, without encountering other stopped samples that have stopped to interact with a pipette or other station. In some embodiments, pipettes may be placed at locations that may access the periphery tracks, for example a movable pipette may be able to access a location on a transverse lane and a location on another transverse lane or the main periphery lane, which may allow priority access to STAT samples, which may bypass local queues on a transverse lane by stopping on the periphery lane.

In this example, the automation tracks are placed in the highest portion of the module, which may allow them to be accessed and serviced from the top of the module. The embodiment shown in FIG. 4A illustrates that an automation track around the periphery of an analyzer module still allow us nearly all of the volume of the analyzer to be utilized for other equipment, such as reagent storage, electrical systems, testing stations, etc. Within module 231, vacant space 252 and 252A is illustrated with a dotted line. Within this space, non-automation track hardware can exist. In this way, even though automation tracks, such as periphery track 232 and transverse track 234, are integrated into the structure of the analyzer module, these tracks do not largely contribute to the overall volume needed for that analyzer module. Similarly, peripheral module 235 can include vacant space 253 which may be used for other purposes, such as storage, or the absent from peripheral module 235, allowing the space to be used for other laboratory purposes, such as waste receptacles or any other useful purposes. In some embodiments space 253 may store automation control hardware and software that enable the lanes of connected modules to operate under control of a central automation controller, allowing movement to be coordinated to act as part of an integrated automation system.

FIG. 4B shows a top view and side view of another module 255 that includes multiple transverse lanes. Periphery lanes 256 and 257 can be linked to other periphery lanes of other modules. Transverse lanes to 60 and 261 intersect these periphery lanes and provide multiple paths between them. When used a standalone mode, module 255 includes a natural loop that may be used to move samples within the module in a manner similar to larger automation systems. The loop may act like a carousel, providing a random access by shifting samples around the loop. Similar to the embodiment shown in FIG. 4A, module 255 includes transport lanes near the top of the module, allowing a plurality of empty regions, 259, 259A, and 259B that may be filled with any hardware for use by the module. It should be understood, that these regions may extend above transport lanes, as well.

The configuration shown in FIG. 4A may also be used to facilitate a standalone mode. Whereas FIG. 3A utilized the return peripheral lane to provide a return lane for a larger collection of modules, the configuration in FIG. 4A can be utilized with a single module 231. When used with a single module, lanes 234 and 235 provide parallel transverse lanes that operator similar to lanes 260 and 261 in FIG. 4B. This dual widthwise lane approach may increase the cost of each module, but the dedicated return lane is incorporated into the footprint of the module, potentially reducing the footprint in a standalone mode and allowing the re-routing capabilities of the integrated system to intrinsically scale as more modules are added, by providing two cut-through paths for each module added to reduce overall congestion. Module 231, in comparison to module 255, may provide a simplified transport mechanism to reduce the cost of manufacturing individual modules, while at the same time allowing a lab to utilize automation accessories such as module 235 to operate module 231 and a standalone mode or as part of a larger automated, multi-module analyzer (e.g., a multi-module mode). It should be appreciated that modules may have more than two transverse lanes, depending on the desired footprint, traffic throughput, or other considerations. Similarly, some embodiments may include more than two lengthwise periphery lanes.

Figure 5:
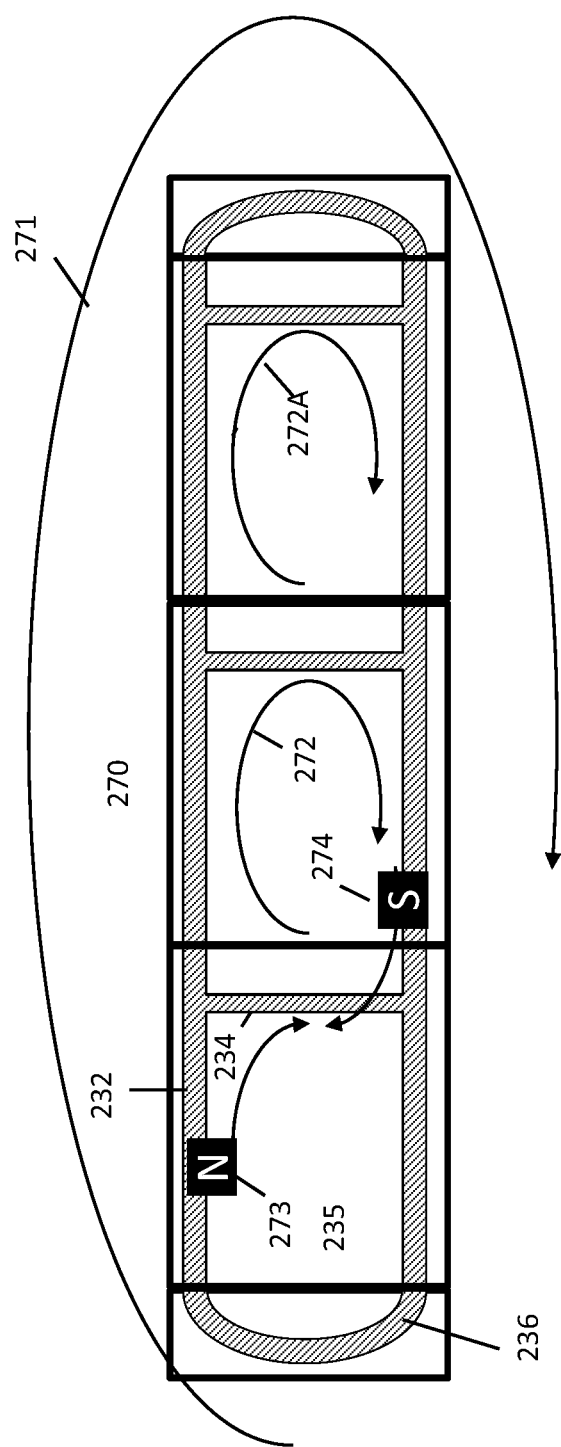
FIG. 5 is a top view of an exemplary analyzer for use with some embodiments that illustrates exemplary traffic flows.

FIG. 5 shows an example use case for a multi-module analyzer composed of a plurality of linked modules. In this example, the periphery track, including each of the local periphery tracks, such as 232, and the return periphery tracks, such as 236, establish a main outer loop around the periphery of the analyzer. This may be used in several ways. For example, in some embodiments, periphery tracks may be configured to be bidirectional tracks. This may enable carriers to move in any direction along the periphery track, arbitrarily under the control of the main automation controller that directs traffic. However, if fast carriers are used, it may be advantageous to create an overall unidirectional traffic flow along the periphery track, regardless of whether the periphery track has unidirectional or bidirectional automation surfaces. For example, a conveyor belt may typically be configured as a unidirectional surface, but may be configured as a bidirectional automation surface by allowing the direction of the rollers to be reversed. Suitable automation surfaces that may provide unidirectional and or bidirectional movement are described throughout.

By providing a unidirectional main traffic flow 271 around the periphery, carriers may move at relatively high speed and with few collisions, as surrounding carriers move in the same direction. Meanwhile, local transverse lanes may operate as unidirectional or bidirectional paths for local traffic, allowing individual carriers to selectively traverse these transverse lanes to reach instruments within the module, such as pipettes. In some embodiments, when local transverse lanes are unoccupied, carriers traversing the main loop 271 may cut through these transverse lanes to create shortcuts if necessary. By providing local paths between the two parallel periphery tracks, a plurality of local traffic loops, such as loop 272 and 272A may be available. These local traffic loops may utilize one or more transverse lanes and any arbitrary portion of the main periphery loop 271.

By way of example, a normal priority sample 273 may utilize the various lanes to access instruments in module 235. Sample 273 may traverse the main periphery loop 271 and while traversing periphery section 230 to be diverted onto local transverse lane 234 to access instruments in module 235. This may be the default route to instruments within module 235 for normal priority samples. Meanwhile, STAT priority samples as is may be given preferred access to resources within the analyzer, such as instruments on transverse lane 234. For example, STAT priority sample 274 may be traversing the main periphery track 271 and need access to a pipette in module 235. In some embodiments, local queues may build up at the instruments within each module, as the instantaneous number of samples that need access to a pipette may be greater than the pipette can service in a short amount of time. STAT sample 274 may enter transverse track 234 from the other end (bottom of the page) from the end than which normal priority samples may enter. This may allow a STAT priority sample to jump to the head of the queue for the local instrument.

Figure 6:
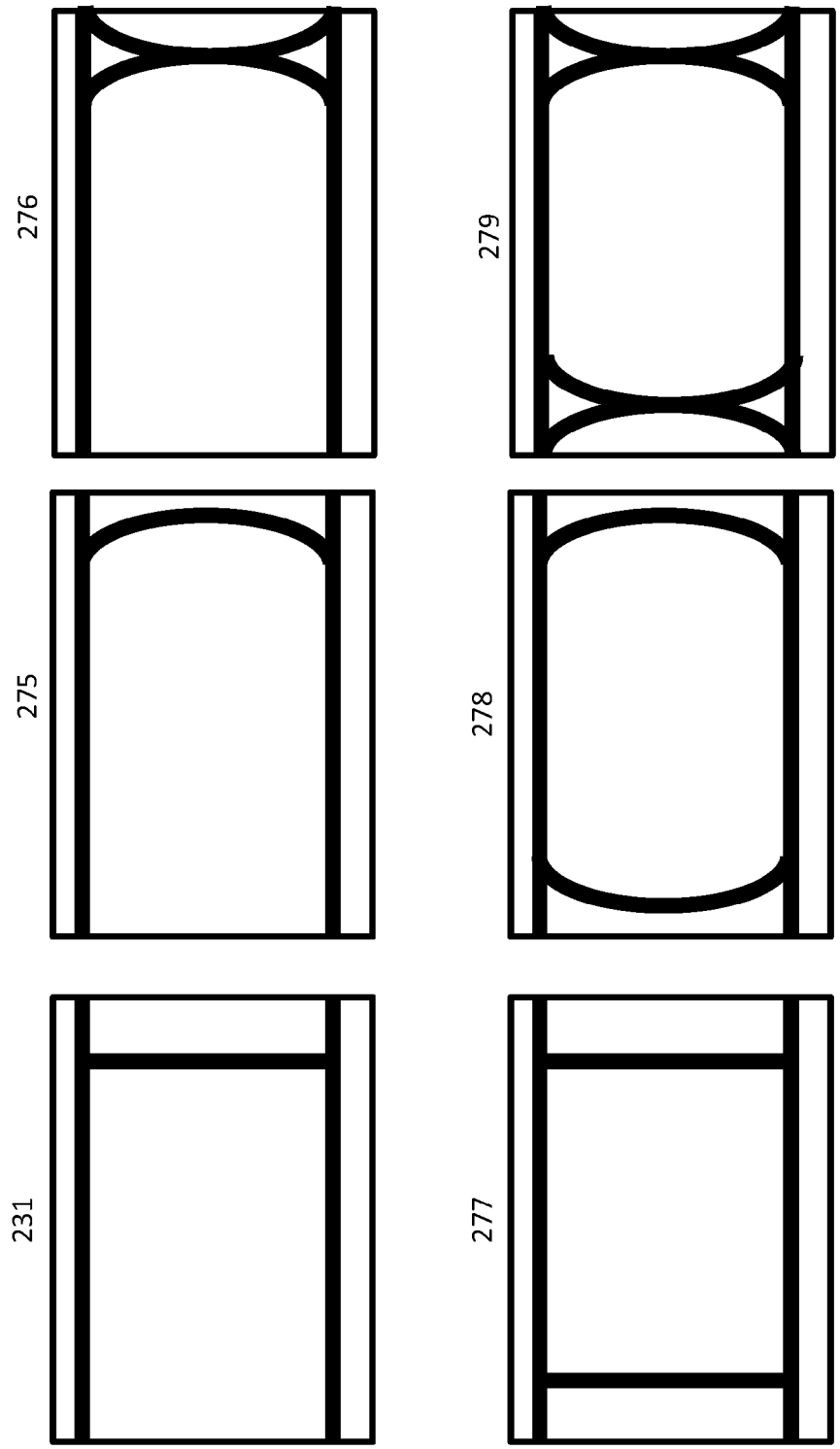
FIG. 6 is a plurality of top views of a plurality of exemplary modules with various transport lane configurations for use with some embodiments.

FIG. 6 shows a plurality of exemplary configurations for transport lanes within an analyzer module. Modules 231, 275, and 276 are examples of modules having two substantially parallel periphery automation surfaces and a single substantially transverse internal automation surface that intersects the two substantially parallel periphery automation surfaces. The periphery automation surfaces include ends that may be accessed on the sides of the module (e.g., ports), allowing these surfaces to be coupled to the periphery automation surfaces of adjacent analyzer modules, allowing modules to be placed into a multi-module system. Modules 277, 278, and 279 are examples of modules with two substantially transverse automation surfaces that link the periphery automation surfaces. These configurations may be useful in a standalone mode, by including a complete loop within the structure of the automation surfaces, allowing continuous motion of samples without additional external hardware. Similarly, ports on the sides may allow the periphery automation surfaces to be coupled to adjacent automation surface of adjacent modules.

Modules in the FIG. 6 illustrate different ways in which the substantially transverse automation surfaces may intersect the periphery automation surfaces. The shape of the intersection may dictate the ways in which sample carriers may be diverted from one automation surface to another. For example, modules 231 and 277 include 90° turns. These turns may be useful to conserve space within the analyzer, but may require that sample carriers slow down or stop before being diverted from the periphery track to a transverse track. The intersections may be referred to as decision points. Decision points in modules 231 and 277 may include mechanical apparatus to divert samples to and from the second track surfaces.

Modules 275 and 278 include intersections that may be described as single branch diverts. These diverts (e.g., decision points) provide a gradual transition from the lengthwise periphery track to the transverse internal track. This curve may allow sample carriers to run between the two tracks without stopping or substantially slowing down. It should be noted, that these curves facilitate motion in one direction (e.g., right to left, bottom periphery track and left to right policy top periphery track, allowing left hand turn when moving counterclockwise, and right hand turns when moving clockwise, but not vice versa). However, these diverts may not be suitable for motion in the other direction of samples are to turn from the periphery track into the transverse track. Embodiment shown in modules 275 and 278 may be most suitable for unidirectional tracks. For example, in module 278, when operated a standalone mode, traffic may be facilitated when moving in a clockwise or counterclockwise internal loop. When operated in a multi-module automation mode, samples may not be able to move directly from the right-hand periphery track to another analyzer module linked to the upper right-hand end of the top periphery track without first making a clockwise loop that utilizes the lower periphery track and left-side transverse track. This limitation may be acceptable if all traffic moves in a clockwise direction, because overall traffic flow may be relatively high and the chance of collision relatively low.

Modules 276 and 279 include intersections that may be described as double branch diverts. Double branch diverts may act like two single branch diverts that facilitate right and left hand turns. This may be well suited for situations in which traffic may locally move bidirectionally. For example, traffic may be moved bidirectionally along the periphery tracks or on the local transverse tracks. In some embodiments, traffic may move unidirectionally on the periphery tracks, providing a large unit directional traffic flow on the periphery of a multi-module configurations, while allowing local motion within each transverse track to be bidirectional. Double branch diverts may allow a sample to move from the top unidirectional periphery track onto a local transverse track or processing. Once a sample has been processed on the local transverse track, the sample may exit the track back onto the top unidirectional periphery track without disrupting the traffic flow. Both right and left hand turns may be facilitated.

It should be appreciated that modules may be coupled to form multi-module configurations in many suitable manners. In the example shown in FIG. 5, periphery tracks are directly coupled, facilitating arrangement of adjacent modules that is substantially linear. However, intervening track sections may also be used, such as straightaways or curves that may allow multiple geometries to be achieved when coupling adjacent modules. For example, curved track sections may be used to couple the ports of periphery tracks for adjacent modules, allowing an elbow to be created, which may allow multiple modules to be placed in a corner of the lab. Similarly, curved and straight sections may be used to link to periphery tracks to more than one adjacent module on each side, allowing modules is placed in a T configuration or a star configuration, to maximize utilization of floor space in the laboratory environment.

Figure 7A:
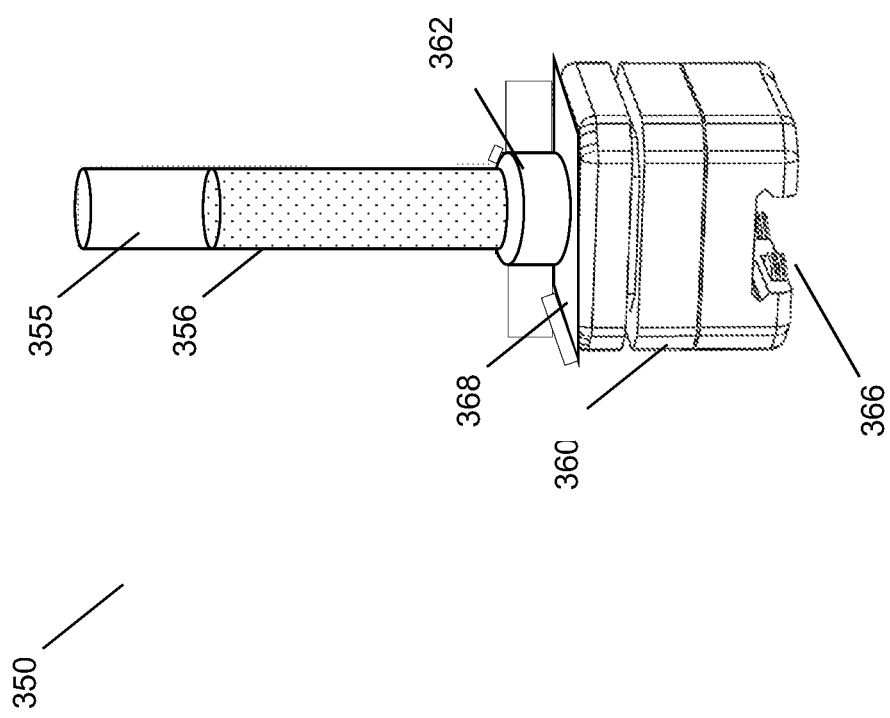
FIG. 7A is a perspective view of an exemplary carrier that can be used with the embodiments disclosed herein.

FIG. 7A depicts an exemplary carrier 350 for use with the present invention. Carrier 350 can hold different payloads in different embodiments. One payload can be a sample tube 355, which contains a fluid sample 356, such as blood or urine. Other payloads may include racks of tubes or reagent cartridges or any other suitable cartridge. Sample carrier 350 includes a main body 360, which can house the internal electronic components describe herein. The main body 360 supports a bracket 362, which can accept a payload. In some embodiments, this is a shallow hole that is designed to accept a fluid container 355 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 362, allowing bracket 362 to act as a universal base for multiple payload types.

Body 360 can include or be coupled to guide portion 366, which allows the carrier 350 to follow a track between decision points. Guide portion 366 can include, for example, a slot to accept one or more rails in the track, providing lateral and/or vertical support. In some embodiments, the guide portion allows the carrier 350 to be guided by walls in the track, such as the walls of a trough-shaped track. The guide portion 366 can also include drive mechanisms, such as friction wheels that allow a motor in the carrier body 360 to drive the carrier or puck 350 forward or backward on the track. The guide portion 366 can include other drive components suitable for use with the embodiments described throughout, such as magnets or induction coils.

Rewritable display 368 can be provided on the top of the carrier 350. This display can include an LCD oriented panel and can be updated in real time by the carrier 350 to display status information about sample 356. By providing the electronically rewritable display on the top of the carrier 350, the status information can be viewed at a glance by an operator. This can allow an operator to quickly determine which sample he/she is looking for when there are multiple carriers 350 in a group. By placing the rewritable display on top of the carrier 350, an operator can determine status information even when multiple carriers 350 are in a drawer or rack.

Figure 7B:
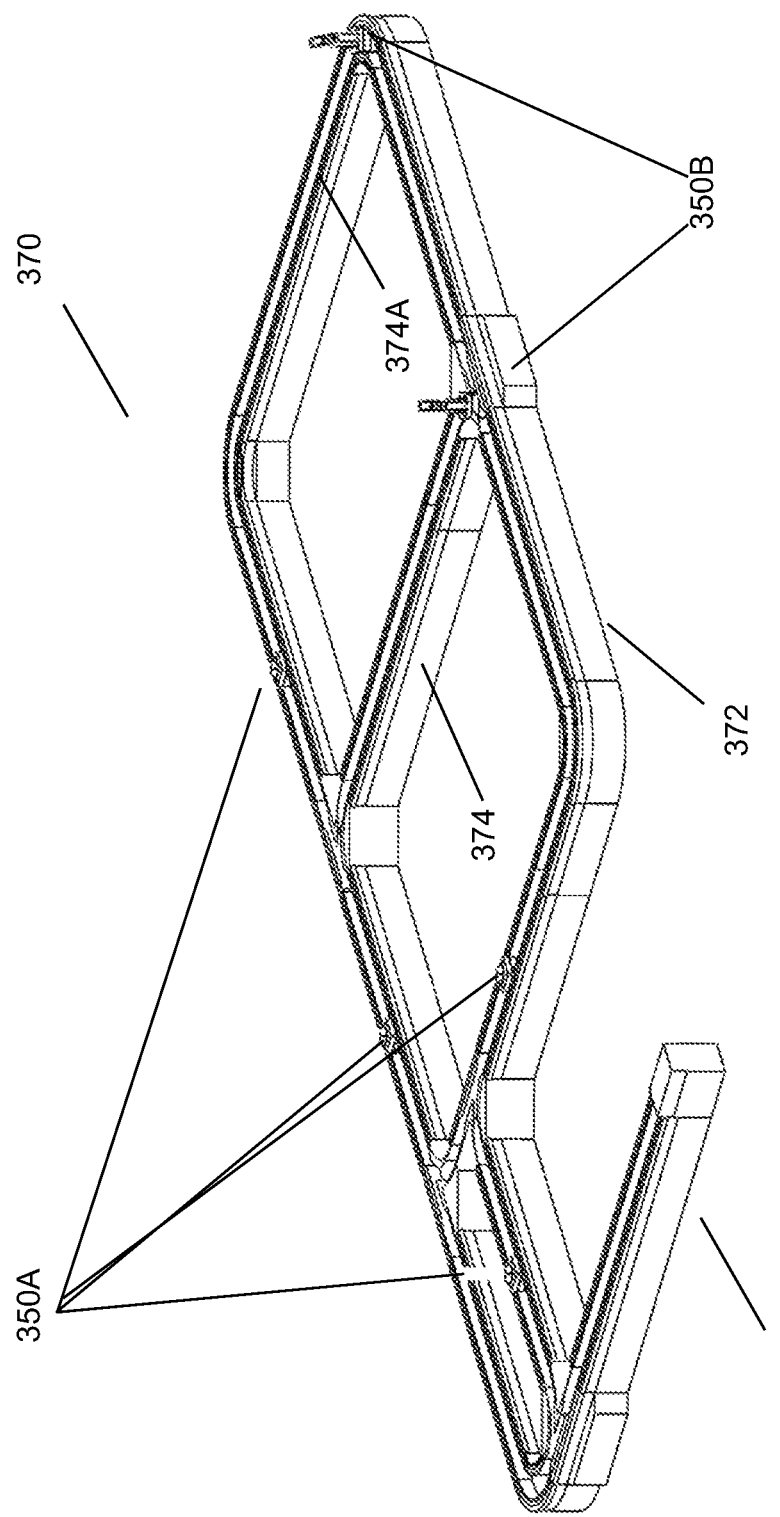
FIG. 7B is a perspective view of an exemplary track configuration that can be used with the embodiments disclosed herein.

FIG. 7B shows an exemplary track configuration 370 for use by carriers 350. In this example, carriers 350A transport sample tubes, while carriers 350B transport racks of tubes along main track 372 and/or subpaths 374 and 374A. Path 376 can be used by an operator to place samples into carriers or remove samples from these carriers.

Figure 7C:
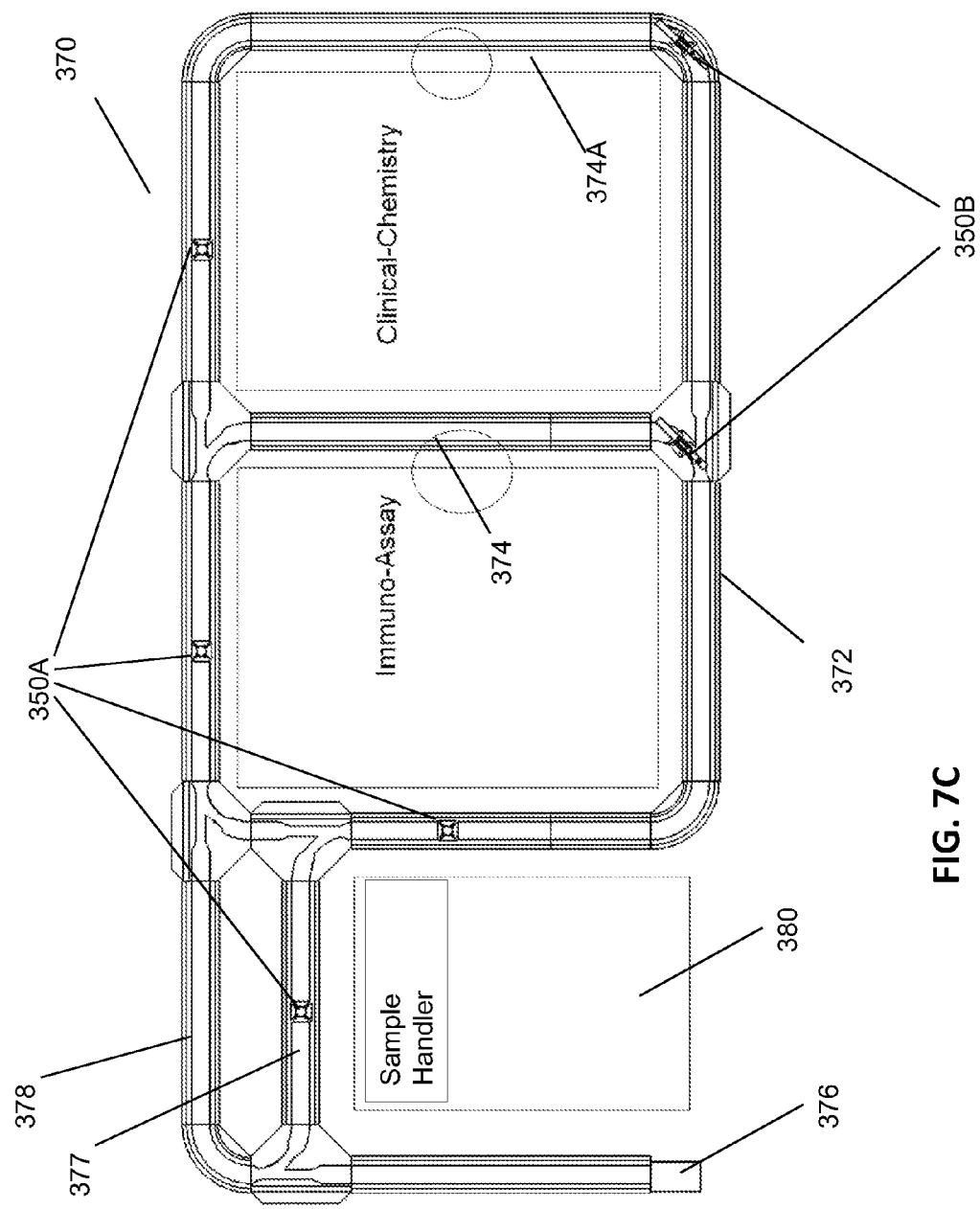
FIG. 7C is a top view of an exemplary automation system that can be used with the embodiments disclosed herein.

FIG. 7C shows an additional view of an exemplary track configuration 370. In this example, sub-path 374 serves an immunoassay station, while sub-path 374A serves a clinical chemistry station. Input/output lane 376 can be served by a sample handler station 380 that uses sub paths 377 and 378 to buffer samples for insertion or removal of the samples from the main track 372.

In some embodiments, the sample handler 380 can also load and unload samples or other payloads to/from the carriers 350A and 350B. This allows the number of carriers to be reduced to the amount needed to support payloads that are currently being used by the stations in track system 370, rather than having a vast majority of carriers sitting idle on tracks 377 and 378 during peak demand for the analyzer. Instead, sample trays (without the carriers disclosed herein) can be placed/removed by an operator at input/output lane 376. This can reduce the overall cost of the system and the number of carriers needed can be determined by the throughput of the analyzer, rather than based on anticipating the peak demand for the analyzer in excess of throughput.

Intelligent Carriers

Embodiments of the present invention can utilize intelligent independent carriers to enable certain improvements over passive pucks on friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in U.S. Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 8:
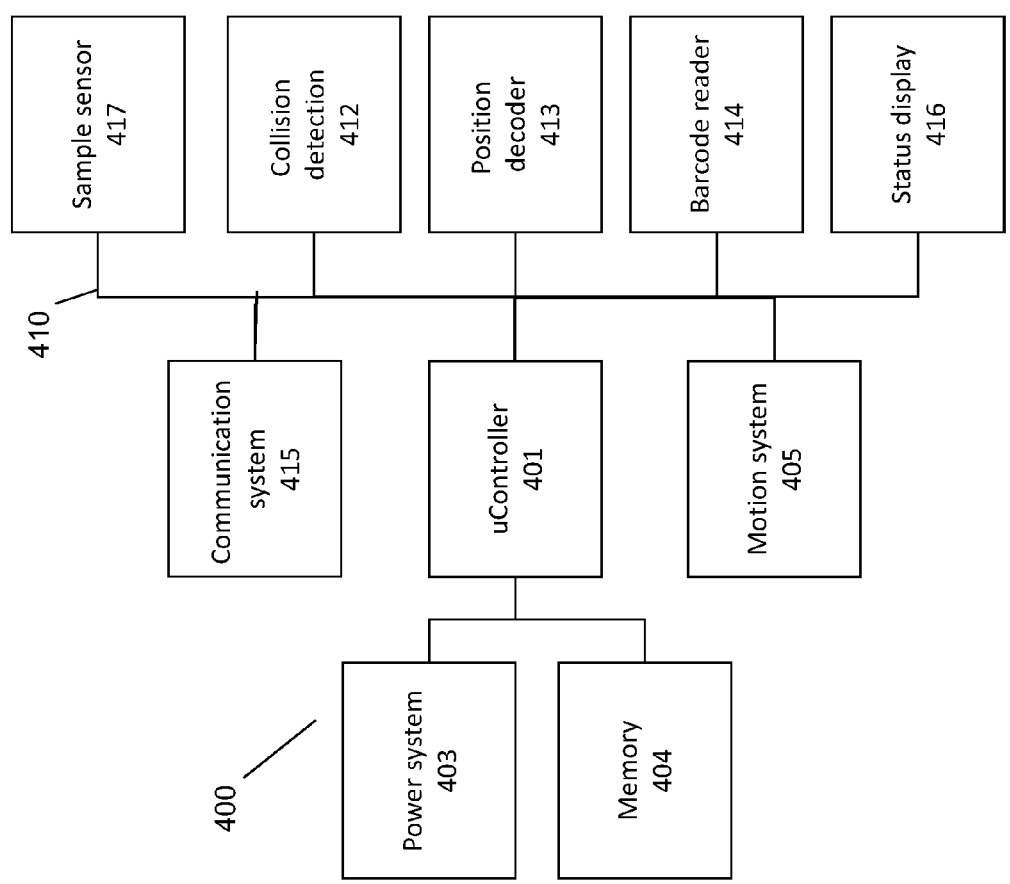
FIG. 8 is a system block diagram of the control systems including onboard active carriers that can be used with certain embodiments disclosed herein.

FIG. 8 shows a top-level system diagram of the control systems and sensors for an exemplary intelligent autonomous carrier 400. Carrier 400 is controlled by a microcontroller 401 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 403 comprises a battery that may be charged as the carrier operates, while in other embodiments, the battery is replaceable or can be manually charged when the carrier is not operating. Power system 403 can include the necessary charging electronics to maintain a battery. In other embodiments, power system 403 comprises a capacitor that may be charged by inductive or electrical contact mechanisms to obtain electrical potential from the track itself, in much the same way a subway car or model train might receive power.

Microcontroller 401 communicates with system memory 404. System memory 404 may include data and instruction memory. Instruction memory in memory 404 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 400, the carrier can keep track of its current status and uses information to intelligently route around the track or convey status information to the track or other carriers.

Microcontroller 401 is responsible for operating the motion system 405, sensors 412, 413, and 414, communication system 415, status display 416, and sample sensor 417. These peripherals can be operated by the microcontroller 401 via a bus 410. Bus 410 can be any standard bus, such as a CAN bus, that is capable of communicating with the plurality of peripherals, or can include individual signal paths to individual peripherals. Peripherals can utilize their own power sources or the common power system 403.

Motion system 405 can include the control logic necessary for operating any of the motion systems described herein. For example, motion system 405 can include motor controllers in embodiments that use driven wheels. In other embodiments, motion system 405 can include the necessary logic to communicate with any active track systems necessary to provide a motive force to the carrier 400. In these embodiments, motion system 405 may be a software component executed by microcontroller 401 and utilizing communication system 415 to communicate with the track. Devices such as motors, actuators, electromagnets, and the like, that are controlled by motion system 405 can be powered by power system 403 in embodiments where these devices are onboard the carrier. External power sources can also provide power in some embodiments, such as embodiments where an LSM provides motive force by energizing coils in the track. In some embodiments, motion system 405 controls devices on or off the carrier to provide motive force. In some embodiments, the motion system 405 works with other controllers, such as controllers in the track, to coordinate motive forces, such as by requesting nearby coils in the track be energized or requesting the movement of local rollers. In these embodiments, motion system 415 can work together with communication system 415 to move the carrier.

Carrier 400 can include one or more sensors. In some embodiments, carrier 400 includes a collision detection system 412. Collision detection system 412 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 400 may be directional, having a front portion and a rear portion. By having a directional geometry, carrier 400 can include a front collision detector and a rear collision detector.

In some embodiments, collision detection information can include information received via the communication system 415. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 400 can also include a position decoder 413. This sensor can extrapolate the carrier's position as described herein. For example, position decoder 413 can include a camera or other optical means to identify landmarks in the track, or observe optical encoding in the track. In some embodiments, position decoder 413 can also include inertial sensors, magnetic sensors, or other sensors sufficient to determine a carrier's current position, direction, velocity, acceleration, and/or jerk.

Carrier 400 can optionally include a barcode reader 414. If equipped with barcode reader 414, carrier 400 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 404 via communication system 415.

Communication system 415 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 415 can include a transceiver and antenna and logic for operating an RF communication protocol. In some embodiments, communication system 415 can also include near field communication, optical communication or electrical contact components. Information conveyed via the communications system to/from carrier 400 is described throughout this application.

In some embodiments, the carrier can also include a status display module 416. The status display module 416 can include a controller and rewritable electronic display, such as an LCD panel or E-ink display. In some embodiments, the controller is treated as an addressable portion of memory, such that the microcontroller 401 can easily update the status display 416.

In some embodiments, the carrier also includes sample sensor 417. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 416.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted on-board each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

FIG. 9 shows an exemplary routing scenario in automation system 500. Carrier 530 receives routing instructions from central management processor 540 via RF signaling. Central management processor 540 can participate in monitoring and directing carriers, including issuing routing instructions and scheduling the movement and dispatch of carriers. Central management processor 540 can be part of the central controller and/or local controllers that interact with individual modules or situations. Central or local controllers can also act at the direction of central management processor 540. Central management processor 540 can include one or more processors operating together, independently, and/or in communication with one another. Central management processor 540 can be microprocessor, software operating on one or more processors, or other conventional computer means suitable for calculating the schedule for multiple carriers within the track system 500.

Central management processor 540 can receive position information from multiple carriers, as well as any sensor information from sensors in the track system 500 and/or information reported by the carriers. Central management processor 540 uses the status information of the carriers and track as well as the identity of samples or other payload carried by the carriers and the required assays to be performed by the system on these samples.

The exemplary track 500 shown in FIG. 9 includes a first curve segment A, that connects to straight segment B and a pullout segment G (e.g., a segment that serves a testing station), which serves analyzer/testing station 205A and pipette 520, via decision point 502. Segment B connects to straight segment C and a pullout segment H, which serves analyzer/testing station 205 and pipette 522, via decision point 504. Segment C connects to curved segment D, which serves sample handling station 205C, and pullout segment I, which serves analyzer/testing station 205B and pipette 524, via decision point 506. Segment D connects to straight segment E and the other end of pullout segment I, via decision point 508. That is, there are different paths between decision points 506 and 508—segments D and I, (where segment I is a pullout that can be used to deliver samples to interact with pipette 524). Segment E connects to straight segment F and the other end of pullout segment H, via decision point 510. Segment F connects to curved segment A and the other end of pullout segment G, via decision point 512. In some embodiments, track 500 includes input and output lanes J and K, which can be used to add or remove carriers at decision points 502 and 512.

In some embodiments, decision points 502-512 are passive forks in the track that carrier 530 can navigate to select a proper destination segment. In other embodiments, decision points 502-512 are active forks that can be controlled by carrier 530 or central management processor 540. In some embodiments, decision points 502-512 are electromagnetically controlled switches that respond to requests by carrier 530, such as via RF or near field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 540 assigns carrier 530 a first route, Route 1, to place the carrier 530 and its payload within reach of pipette 520. Carrier 530 is instructed to travel along segment J to decision point 502 and travel onto segment G to stop at a position accessible to pipette 520. In some embodiments, carrier 530 receives the instructions and determines its current location and trajectory to determine a direction and trajectory to use to reach decision point 502. Carrier 530 can also take into account that it will be making a hard right turn at decision point 502 onto segment G. In some embodiments, decision point 502 includes a switching mechanism in the track that can operate under the control of carrier 530. In these embodiments, carrier 530 communicates with the track on approach to decision point 502 to request switching onto segment G. In other embodiments, carrier 530 may have a steering mechanism (such as moveable guide wheel, directional magnets, asymmetric brakes, or the like) that allows carrier 530 to make a right turn onto segment G at decision point 502, without the assistance of an external gate integrated into the track. In these embodiments, carrier 530 engages the steering mechanism at decision point 502 to make the turn onto segment G.

Carrier 530 can determine its rough location—its current track section, such as section J, by reading encoding in the track, such as optical encoding, or RFID tags. In some embodiments, carrier 530 uses multiple means to determine its location within the track system 500. For example, RFID tags can be used to determine generally on which track segment the carrier 530 is located, while optical encoding or other precise encoding can be used to determine the position within that track segment. This encoding can also be used to determine velocity, acceleration, or jerk by observing changes in the encoding (e.g., derivatives from the position information).

Carrier 530 can use the identification of the current track section to determine the appropriate route to the destination section either by explicit instruction received by the central management processor 540 or by looking up an appropriate route in an onboard database in memory 404, as shown in the onboard control systems in FIG. 8. In some embodiments, the carrier 530 has an understanding of how to reach section G from section J based on a map stored in the memory of carrier 530 in memory 404. This map can include a simple lookup table or a tree of track sections where each node is linked by the corresponding decision points, or vice versa. For example, upon identifying that the carrier is currently in the track section J, the onboard database can inform carrier 530 to proceed to decision point 502 to be switched to the right onto section G.

As shown in FIG. 9, carrier 530 responds to instructions for Route 1 by proceeding onto section G and stopping at a position near pipette 520. Once the carrier 530 is stopped, it can receive additional instructions from the analyzer/testing station controlling pipette 520. For example, analyzer 205A can control pipette 520 and can instruct carriers on section G to position themselves at precise points along section G. This allows analyzer/testing stations to treat track sections as random access queues. For example, once carrier 530 stops on section G, additional instructions can be conveyed via central management processor 540 or directly from analyzer 205A to the carrier 530 via RF transmission or other means, such as local optical or inductive/near field signals. These instructions can include halting while another carrier interacts with pipette 520, and subsequently proceeding to a position accessible to pipette 520, when analyzer 205A is ready to perform one or more assays on the sample carried by carrier 530.

Once analyzer/testing station 205A has finished interacting with the sample carried by carrier 530, additional routing instructions can be sent to the carrier 530 from the central management processor 540. For example, Route 2 can include routing instructions to proceed to section H to interact with pipette 522. In some embodiments, the routing tables contained within onboard memory 404 of carrier 530 have sufficient information about the track layout to allow the carrier to route itself to section H. In other embodiments, a list of routing steps can be transmitted to carrier 530 via central management processor 540. It will be appreciated that other embodiments can include conveying any subset of the route to carrier 530 and/or sending routing instructions in a piecemeal fashion, such that carrier 530 always knows the next routing step, and optionally subsequent routing steps.

In this example, carrier 530 receives a route list representing Route 2 from central management processor 540 instructing it to proceed via section G to decision point 512. At decision point 512, carrier 530 will initiate switching onto section A by interacting with a gate or by turning as described above. Carrier 530 can take into account curved track conditions on section G and section A to ensure that acceleration and jerk conditions do not exceed a threshold requirement for the sample it carries. This can prevent spillage or instability during transit. The route information received by carrier 530 then instructs carrier 530 to proceed through decision point 502 without turning. The trajectory used in Route 2 when approaching decision point 502 can be different (e.g., faster) from that used during Route 1, because carrier 530 knows that it does not need to make a sharp right turn onto section G. In some embodiments, this allows carrier 530 to approach decision point 502 with a substantially greater velocity during Route 2 than during Route 1. By traversing decision point 502 faster if carrier 530 is not turning, carrier 530 can complete Route 2 in less time than embodiments in which carrier 530 must slow down for possible switching at each decision point. This is an improvement over the prior art, where carriers are typically halted and singulated, regardless of whether the carrier is turning or not.

After passing decision point 502, carrier 530 proceeds onto section B. At decision point 504, carrier 530 proceeds to section C. At decision point 506, carrier 530 prepares and turns onto section I, where it stops for interaction with pipette 524. Like section G, section I can act as a queue for pipette 524 and carrier 530 can be controlled under local instruction by the analyzer/testing station 205B served by section I.

When pipette 524 is done interacting with carrier 530, central management processor 540 can provide new routing instructions to carrier 530 instructing carrier 530 to proceed onto an output path K. Route 3 can be handled in the same manner as Route 1 and Route 2. Upon receiving instructions for Route 3, carrier 530 proceeds down section I to decision point 508 where it turns back onto a main track section E and proceeds past decision point 510, track section F, and decision point 512 (without needing to slow down in some embodiments), and onto section K where the carrier 530 and/or the sample can be removed from the system by an operator. Carrier 530 can then be reused for samples at input section J. Upon receiving instructions for Route 4, carrier 530 proceeds down section D to sample handling station 205C and to decision point 508 where it turns back onto a main track section E and then proceeds the same as Route 3.

In some embodiments, each track section of FIG. 9 can be configured to include one or more speed zones. This may be represented as a speed or acceleration limit in software that maintains motion profiles for each carrier. For example, section D may be represented for trajectory control as a slow speed zone for all carriers to account for the inherent centripetal forces exerted by the track as carriers traverse section D. Similarly, track sections can include multiple speed zones within the track section, which may include motion profile rules. For example, a carrier may slow down responsive to software enforcement of rules that identify the latter portion of section C as a braking zone due to the upcoming speed limited zone in track section D. In some embodiments, software responsible for maintaining motion profile rules for carriers may take into account an upcoming speed zone and brake in an unlimited track section in anticipation. Furthermore, different track section portions can be represented as dynamic speed zones. For example, a stopping point for interaction with a pipette can be represented a speed zone with a speed of zero for carriers that should stop at that location. This may allow trajectory enforcing software to automatically slow down the affected carrier as it approaches the stopping position.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An integrated automation system for use in transporting patient samples between modules, the system comprising:
a plurality of in vitro diagnostic analyzer modules configured to perform in vitro diagnostic analysis of aspirated portions of patient samples the modules being mechanically coupled to one another, each of the plurality of modules comprising an internal transport system and a testing station that includes a pipette configured to aspirate a portion of patient samples transported via the internal transport system and analytical equipment configured to perform an assay on the aspirated portion where each internal transport system is configured to transport the samples into and out of each module to which the transport system is internal and selectively to and from the pipette and each internal transport system comprises:
a pair of parallel periphery track portions physically integrated within one of the plurality of analyzer modules, where each of the periphery track portions has two ends and is configured to transport the samples in at least a direction opposite each respective other periphery track portion of the pair, and
one or more bidirectional transverse track portions integrated within the analyzer module and accessible to the pipette, the one or more transverse track portions intersecting the pair of periphery track portions to form an internal path within the analyzer module between the periphery track portions that facilitates selective transport of the samples to the pipette for aspiration of a portion of each sample,
wherein the ends of the periphery track portions of adjacent modules are mechanically coupled to one another, thereby forming a continuous periphery track running through and connecting the plurality of modules that includes a continuous loop around the analytical equipment of the plurality of in vitro diagnostic analyzer modules, and
wherein the samples are transported along the continuous periphery track and the transverse track portions of the plurality of modules, the continuous periphery track and the transverse track portions forming a plurality of paths along which the samples are transported.

2. The integrated automation system of claim 1, wherein each of the plurality of modules further comprises a first side, a second side opposite the first side, a front side extending between the first side and the second side, and a back side opposite the front side and extending between the first side and the second side, wherein the first side and the second side are spaced apart from one another, wherein the front side and the back side are spaced apart from one another,
  wherein each pair of periphery track portions of the plurality of modules comprises a first periphery track portion extending from the first side to the second side proximate the front side of the respective module, and a second periphery track portion extending from the first side to the second side proximate the back side of the respective module,
  wherein each of the one or more transverse track portions integrated within the respective module extends between and intersects the first periphery track portion and the second periphery track portion, and
  wherein the plurality of paths formed by the continuous periphery track and the one or more transverse track portions comprise a plurality of continuous loops when the internal transport systems of respective modules are connected to one another.

3. The integrated automation system of claim 1, further comprising:
  one or more dedicated return lane modules configured to couple to an end module of the plurality of modules, each dedicated return lane module comprising two return ends, each configured to mechanically couple to respective ends of the two periphery track portions of the end module, each dedicated return lane configured to thereby link the pair of periphery track portions of the end module and form part of the continuous periphery track.

4. The integrated automation system of claim 3, wherein at least one dedicated return lane module further comprises dedicated input and output track portions.

5. The integrated automation system of claim 1, wherein each intersection of the transverse track portions with each respective periphery track portion comprises one of (i) a sharp intersection; (ii) a gradual curved intersection; and (iii) a double-branch, gradual curved intersection that provides a right and left hand branch between the respective rack portions.

6. The integrated automation system of claim 5, wherein each intersection of the one or more transverse track portions with the pair of periphery track portions comprises the gradual curved intersection, and wherein the samples are transported uni-directionally.

7. The integrated automation system of claim 5, wherein each intersection of the one or more transverse track portions with the pair periphery track portions comprises the double-branch, gradual curved intersection, and wherein the samples are transported bi-directionally.

8. The integrated automation system of claim 1, wherein the analytical equipment comprises one of an immunoassay station and a clinical chemistry station.

9. The integrated automation system of claim 1, wherein each of the plurality of modules is capable of stand-alone operation when not connected to other of the plurality of modules.

10. The integrated automation system of claim 1, comprising a controller configured to selectively divert samples from the continuous periphery track to one of the one or more transverse track portions for processing by an instrument on the respective module.

11. The integrated automation system of claim 10, wherein the controller is further configured to selectively divert a prioritized sample to one of the one or more transverse track portions for processing by the respective module by transporting samples preceding the prioritized sample along the continuous periphery track.

12. A method of transporting samples between modules, the method comprising:
  providing each of a plurality of modules mechanically coupled to one another, each including a pipette configured to aspirate a portion of patient samples transported via an internal transport system and analytical equipment configured to perform an assay on the aspirated portion,
  providing the internal transport system integrated within each of the plurality of modules;
  providing as part of the internal transport system in each module, two parallel periphery track portions physically integrated within a respective one of the plurality of modules, each of the periphery track portions having two ends and configured to transport the samples in at least a direction opposite the other periphery track portion; and
  providing as part of the internal transport system in each module, one or more bidirectional transverse track portions integrated within the respective module, the one or more transverse track portions intersecting the two periphery track portions to form an internal path within the respective module accessible to the pipette for aspirations,
  wherein the internal transport systems in each module are mechanically coupled to one another, thereby forming a loop of continuous periphery track around the analytical equipment and running through and connecting the plurality of modules, and
  wherein the continuous periphery track and the one or more transverse track portions form a plurality of paths along which the samples are transported.

13. The method of claim 12, wherein each of the plurality of modules has a first side, a second side opposite the first side, a front side extending between the first side and the second side, and a back side opposite the front side and extending between the first side and the second side, wherein the first side and the second side are spaced apart from one another, wherein the front side and the back side are spaced apart from one another,
  wherein each of the plurality of modules comprises two periphery track portions, a first periphery track portion extending from the first side to the second side near the front side of the respective module, and a second periphery track portion extending from the first side to the second side near a portion proximate the back side of the respective module,
  wherein each of the one or more transverse track portions integrated within the respective module extends between and intersects the first periphery track portion and the second periphery track portion, and
  wherein the plurality of paths formed by the continuous periphery track and the one or more transverse track portions comprise a plurality of continuous loops when the internal transport systems of respective modules are connected to one another.

14. The method of claim 12, further comprising:
  providing one or more dedicated return lanes, each dedicated return lane having two return ends, each dedicated return lane configured to be connected to the continuous periphery track via a first of the two return ends and a second of the two return ends connecting to one end of respective adjacent periphery track portions.

15. The method of claim 12, wherein the intersection of the one or more transverse track portions with at least one of the one or more periphery track portions comprises one of (i) a sharp intersection, (ii) a gradual curved intersection: and (iii) a double-branch gradual curved intersection.

16. The method of claim 15, wherein the intersection of the one or more transverse track portions with at least one of the one or more periphery track portions comprises the gradual curved intersection, and wherein the samples are transported uni-directionally.

17. The method of claim 15, wherein the intersection of the one or more transverse track portions with at least one of the one or more periphery track portions comprises the double-branch gradual curved intersection, and wherein the samples are transported bi-directionally.

18. The method of claim 12, wherein at least a subset of the plurality of modules comprises in vitro diagnostics modules, and wherein the samples comprise patient samples.

19. The method of claim 12, wherein the modules comprise one or more of (i) a sample handling module; (ii) an immunoassay module; and (iii) a clinical chemistry module.

20. The method of claim 12, wherein each of the plurality of modules is capable of stand-alone operation when not connected to other of the plurality of modules.

* * * * *